United States Patent [19]

Berlin et al.

[11] Patent Number: 4,692,153
[45] Date of Patent: Sep. 8, 1987

[54] SURGICAL WOUND DRAIN DEVICE

[76] Inventors: Richard B. Berlin; Richard B. Berlin, Jr., both of 309 Engle St.; Stephen L. Javna, 163 Engle St., all of Englewood, N.J. 07631

[21] Appl. No.: 847,704

[22] Filed: Apr. 3, 1986

[51] Int. Cl.⁴ .............................................. A61M 25/00
[52] U.S. Cl. ................................... 604/171; 604/280; 604/21; 604/93
[58] Field of Search ................. 604/171, 158, 53, 264, 604/280, 21, 117, 93

[56] References Cited

U.S. PATENT DOCUMENTS

| | | | |
|---|---|---|---|
| 2,407,929 | 9/1946 | Jeckel | 7/11 |
| 3,144,868 | 8/1964 | Jascalevich | 128/350 |
| 3,406,691 | 10/1968 | Kettenbach | 128/350 |
| 3,430,631 | 3/1969 | Abramson | 128/350 |
| 3,815,608 | 6/1974 | Spinosa et al. | 128/349 R |
| 3,840,008 | 10/1974 | Noiles | 604/117 |
| 4,168,699 | 9/1979 | Hauser | 604/171 |
| 4,257,422 | 3/1981 | Duncan | 128/350 R |
| 4,398,910 | 8/1983 | Blake et al. | 604/93 |
| 4,445,897 | 5/1984 | Ekbladh et al. | 604/280 |
| 4,465,482 | 8/1984 | Tittel | 604/280 |

Primary Examiner—C. Fred Rosenbaum
Assistant Examiner—John D. Ferros
Attorney, Agent, or Firm—DePaoli & O'Brien

[57] ABSTRACT

This invention provides a surgical wound drain device which is adapted for postoperative multiphasic suction withdrawal of physiological fluids and coagulated solids and tissue debris from a wound cavity in a closed drainage system.

The drain device consists of an inner catheter member, and an outer tubular member which has one or more thin pliable strips extending form the distal end periphery. The catheter withdraws accumulated body fluids in a postoperative first stage. The catheter is removed, and the remaining outer tubular member with its extended pliable strips is adapted to withdraw body fluids and coagulated solids and tissue debris in a second stage over an extended period.

14 Claims, 9 Drawing Figures

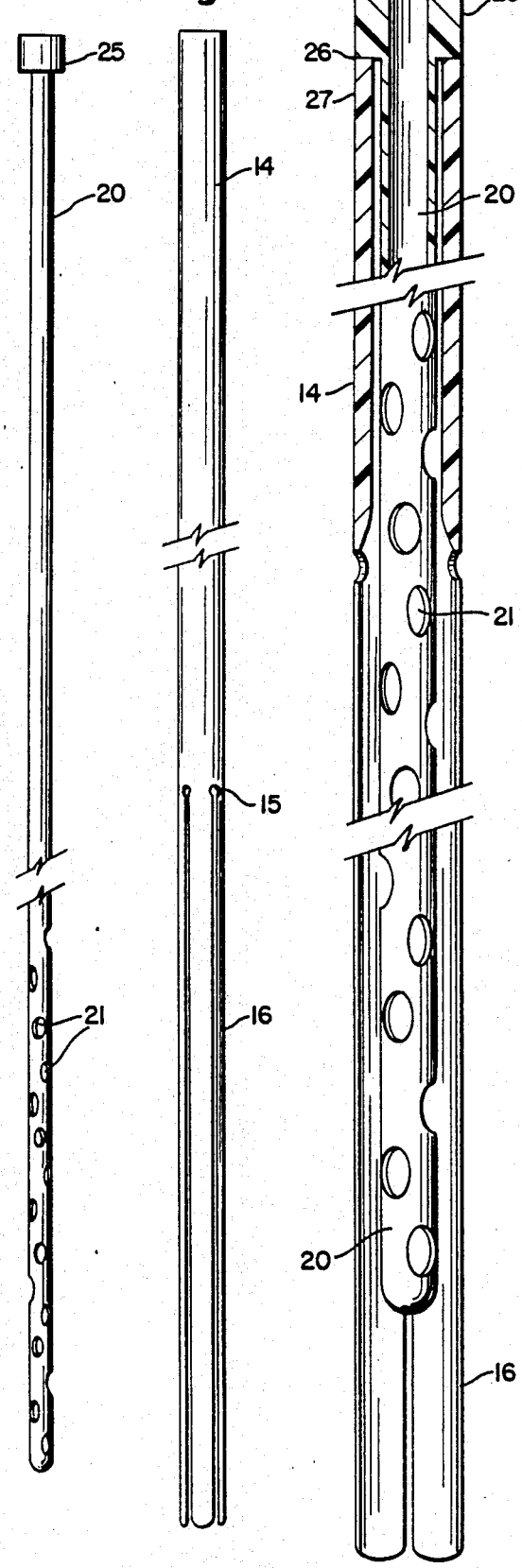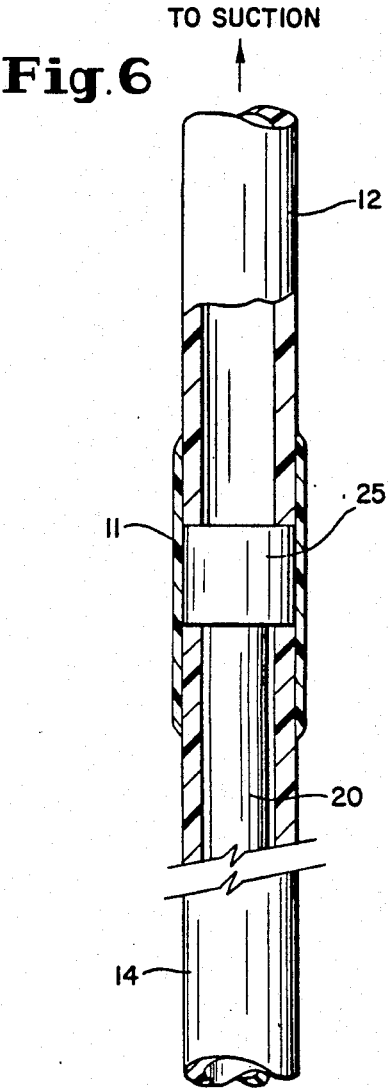

SURGICAL WOUND DRAIN DEVICE

BACKGROUND OF THE INVENTION

Surgical wounds have been drained for many years by a variety of devices which are generally classified at the present time as "open" or "closed". Drainage systems are intended to evacuate blood, serum, pus, bile or other biological fluids which can accumulate in the depths of a wound or cavity and lead to various complications. Most widely employed are the "closed" systems which are designed to provide a conduit from the cavity through a tightly fitting perforation of the skin and subcutaneous tissues to an outside reservoir which draws fluids out with negative pressure. The system is closed to outside bacterial contamination in order to minimize the risk of inadvertent infection. Construction has generally been of semi-rigid or elastic tubular material, with perforations to allow body fluid to enter the tube. If it is necessary to drain more than one area simultaneously, then multiple drains have been required.

Surgical drains have also been classified as "active" and "passive". Active drains depend upon negative pressure to aspirate wound contents. Passive drains depend upon capillary action along the drain surfaces aided by fluctuation in intra-abdominal or intrathoracic pressures induced by respiration or body motion.

Surgical wound drains usually exhibit one or more deficiencies in conventional use. Some surgical drain devices permit ingress of bacteria into a wound cavity, and most drain devices become occluded by blood clots or accretions of coagulated protein mass or tissue debris, which results in premature termination of effective drainage function.

Many surgical drain devices have internal ridges or step-offs which provide the nidus for a build-up of clots along the hydraulic outflow pathway of wound or body cavity fluids, with resultant early obstruction of the drainage flow and failure to accomplish the primary function of complete fluid removal.

From a more fundamental viewpoint, the known surgical drain devices have not been designed with recognition of wound drainage as a multiphasic process and therefore the devices lack the versatility to satisfy the requirements of the multiphasic wound drainage process.

The earliest phase of wound evolution is an outpouring of liquid blood, serum, bile, intestinal digestive juices, and the like, including air. Shortly thereafter blood clots and inspissated fluids develop, followed by purulent material containing white blood cells, tissue debris, and bacteria.

Accordingly, it is an object of this invention to provide a polyfunctional surgical drain device for closed suction drainage systems.

It is another object of this invention to provide a surgical drain device which is adapted to accomplish long term wound drainage without premature clogging and wound fluid outflow stoppage.

It is a further object of this invention to provide a surgical drain device which is designed to satisfy the requirements of surgical wound drainage as a multiphasic process, capable of evacuating blood fluid before it clots, and clotted blood, body fluids, and tissue debris.

Other objects and advantages of the present invention shall become apparent from the accompanying description and drawings.

U.S. patents of general interest with respect to the present invention include U.S. Pat. Nos. 2,407,929; 3,406,691; 3,430,631: 3,815,608; 4,398,910; 4,445,897; and 4,465,482.

SUMMARY OF THE INVENTION

One or more objects of the present invention are accomplished by the provision of a polyfunctional surgical wound drain device which comprises an outer elongated flexible tubular member and a detachably removable inner elongated flexible tubular member which is in a coextensive and slidable relationship with the outer tubular member, wherein the outer tubular member has one or more (e.g., 2-5) thin pliable tail strips extending from the distal end periphery, and the inner tubular member is a catheter with a central lumen and a plurality of perforated drainage ports and with the distal end extending beyond the distal end of the outer tubular member, and the catheter has a rim-flanged proximal end which is in abutting contact with the proximal end periphery of the outer tubular member.

In another embodiment, this invention provides a polyfunctional surgical drain device for a closed wound drainage system which comprises (1) an outer elongated flexible tubular member (2) a detachably removable inner elongated flexible tubular member which is in a coextensive and slidable relationship with the outer tubular member, wherein the outer tubular member has one or more thin pliable tail strips extending from the distal end periphery, and the inner tubular member is a catheter with a central lumen and a plurality of perforated drainage ports and with the distal end extending beyond the distal end of the outer tubular member, and the catheter has a rim-flanged proximal end which is in abutting contact with the proximal end periphery of the outer tubular member; and (3) a hollow sleeve member with an end which forms a sealed attachment to the abutting proximal ends of the tubular members, and with an end which is adapted to connect with a suction drainage fluid reservoir.

In a further embodiment, this invention provides a polyfunctional surgical wound drainage system which comprises (1) an outer elongated flexible tubular member; (2) a detachably removable inner elongated flexible tubular member which is in a coextensive and slidable relationship with the outer tubular member, wherein the outer tubular member has one or more thin pliable tail strips extending from the distal end periphery, and the inner tubular member is a catheter with a central lumen and a plurality of perforated drainage ports and with the distal end extending beyond the distal end of the outer tubular member, and the catheter has a rim-flanged proximal end which is in abutting contact with the proximal end periphery of the outer tubular member; and (3) a suction drainage fluid reservoir which is attached to the abutting proximal ends of the tubular members with a hollow sleeve means that forms a sealed connection for a vacuum-tight system.

BRIEF DESCRIPTION OF THE DRAWINGS

FIG. 3 is a view of the inner tubular catheter member distal end drainage ports of an invention surgical drain device.

FIG. 4 is a view of the outer tubular member with three thin pliable tail strips of an invention surgical drain device.

FIG. 5 is an enlarged fragmentary cross-section of the integrated assembly of inner and outer tubular members of an invention surgical drain device.

FIG. 6 is a view of the abutting contact of the proximal ends of the inner and outer tubular members of an invention surgical drain device, with the proximal ends integrally attached to a suction fluid drainage system by means of a hollow sleeve member.

DETAILED DESCRIPTION OF INVENTION EMBODIMENTS

Figure 1:
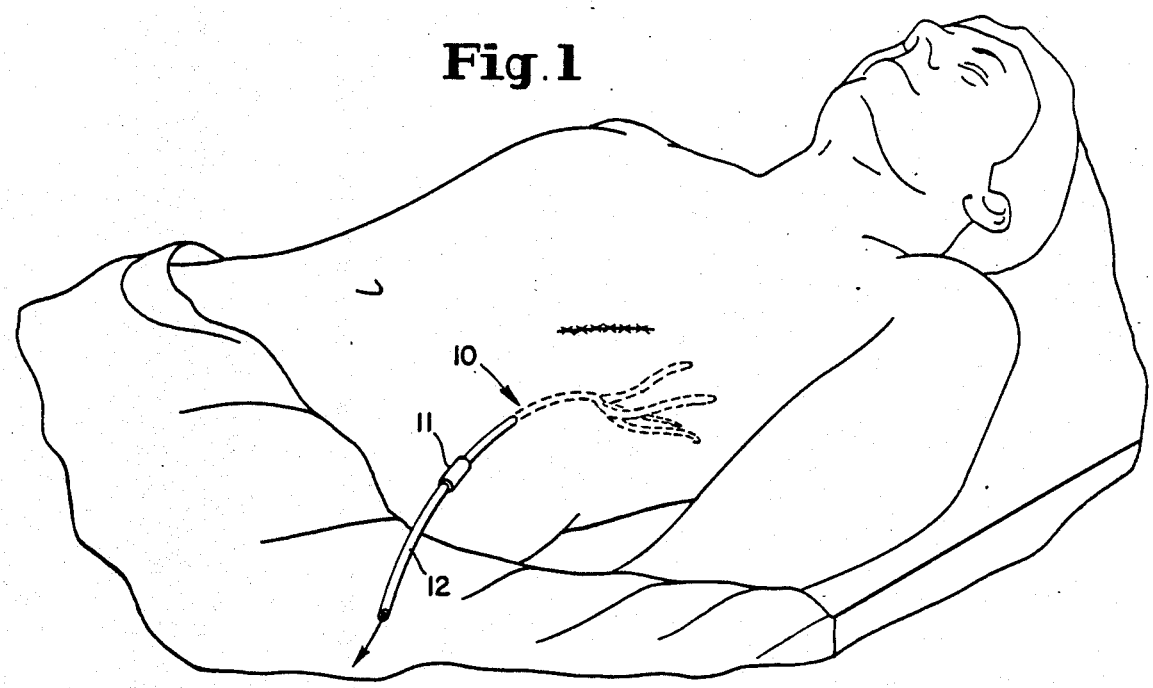
FIG. 1 is a view of a postoperative patient with an invention surgical drain device situated in a wound cavity.

A present invention surgical wound drain is a polyfunctional device which is adapted to achieve multiphasic suction drainage of postoperative biological fluids and particulate solids from a wound cavity in a human body.

Thus, in a further embodiment this invention provides a process for multiphasic surgical wound drainage which comprises (1) connecting a suction drainage fluid reservoir to a drain device which is inserted in a surgical wound cavity, wherein said drainage device comprises an outer elongated flexible tubular member and a detachably removable inner elongated flexible tubular member which is in a coextensive and slidable relationship with the outer tubular member, wherein the outer tubular member has one or more thin pliable tail strips extending from the distal end periphery and radially distributed within the wound cavity zone, and the inner tubular member is a catheter with a central lumen and a plurality of perforated drainage ports and with the distal end extending beyond the distal end of the outer tubular member, and the catheter has a rim-flanged proximal end which is in abutting contact with the proximal end periphery of the outer tubular member; (2) applying suction to the drain device to withdraw postoperative body fluids from the wound cavity through the catheter member: (3) disconnecting the suction drainage fluid reservoir from the drain device, and detaching and removing the catheter out of the central lumen of the outer tubular member; and (4) connecting the suction drainage fluid reservoir to the proximal end of outer tubular member of the drain device which remains inserted in the wound cavity, and applying suction to the said tubular member of the drain device to withdraw postoperative body fluids and coagulated blood and particulate tissue solids along the spaced paths of the tail strips and through the lumen of said tubular member.

A present invention surgical drain device has physical dimensions which are suitable for manipulation and placement in a wound cavity that is located in an internal zone or tissue space of a human body.

Depending on the location and type of postoperative wound cavity, a present invention surgical drain device 10 outer and inner tubular members as shown in the Figures can have a length between about 10–50 centimeters.

The outer tubular member 14 in the Figures can have an outer dimension between about 3–20 millimeters, with a wall thickness between about 0.5–3 millimeters. The pliable tail strips 16 can have a length between about 5–20 centimeters, a width between about 0.1–3 centimeter, and a thickness between about 0.1–3 millimeters. The pliable tails can also be annular in cross-section.

Inner tubular member 20 (i.e., the catheter) in the Figures has an outer dimension which is less than the inner cross-section dimension of outer tubular member 14, with a wall thickness between about 0.5–2 millimeters.

A present invention surgical drain device preferably is constructed of biocompatible polymeric materials. Suitable materials include synthetic polymers such as polyethylene, polypropylene, polybutylene, polystyrene, polyvinyl chloride, polyvinylidene fluoride, polytetrafluoroethylene, polyurethane, silicone elastomer, polybutadiene copolymer elastomer, poly(ethylene-vinyl acetate), polycarbonate, and the like.

Illustrative of a present invention surgical drain device, outer tubular member 14 in the Figures is constructed with a flexible material such as silicone elastomer. Inner tubular member 20 has lateral flexibility and is constructed with a resilient material such as polyvinyl chloride. Thin tail strips 16 are constructed with a pliable material such as polyethylene, polyurethane or silicone elastomer. An invention surgical drain device typically has 2–5 thin pliable tail strips 16, and most preferably has at least three tail strips.

Referring to the Figures, in FIG. 1 surgical drain device 10 is positioned in a wound cavity. Surgical drain device 10 is attached by means of hollow sleeve 11 to conduit member 12 of a closed suction drainage fluid reservoir which is not shown. The lumen pathway for the wound drain fluid in surgical drain device 10 is smooth walled and ridge-free. Similarly, the outer surface of surgical drain device 10 has a smooth and ridge-free construction, which facilitates removal of the device from a cavity after the drainage function is completed.

Figure 2:
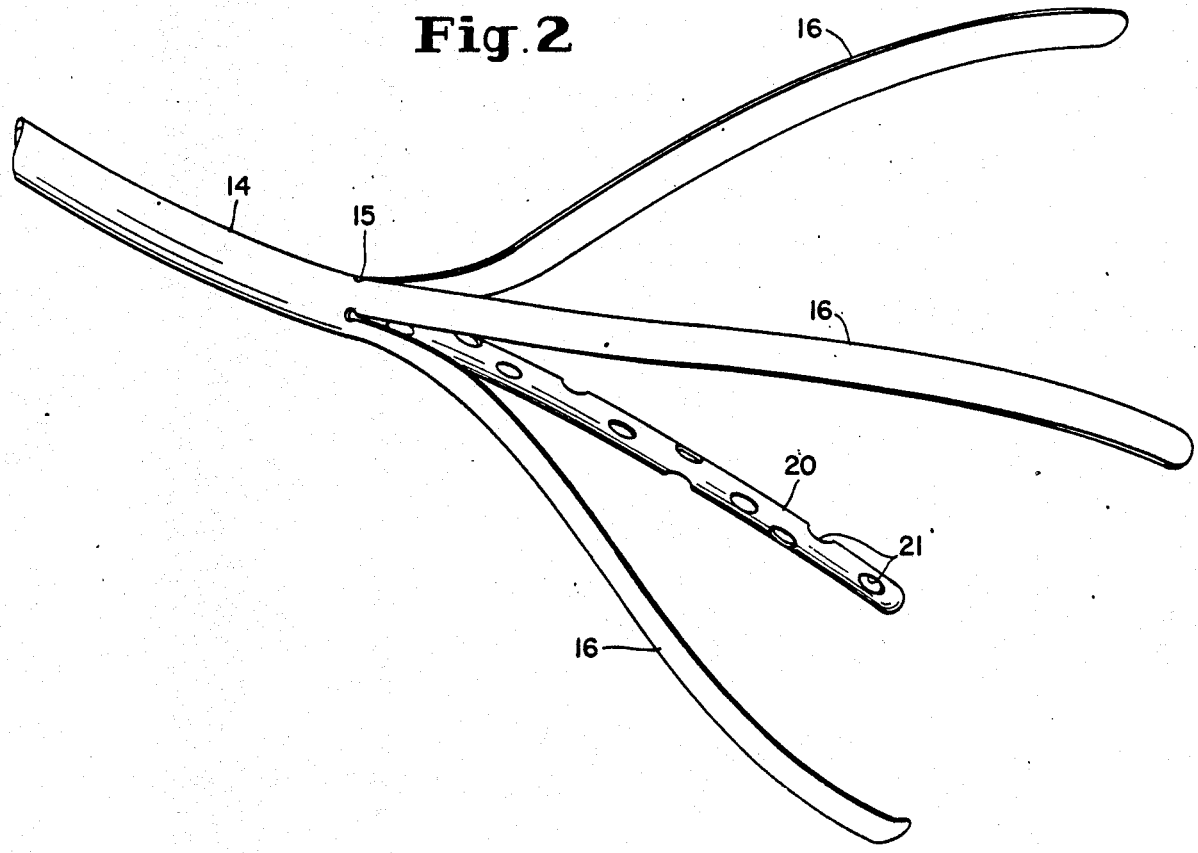
FIG. 2 is an enlarged view of the coextensive distal ends of the inner and outer tubular members of an invention surgical drain device.
Figure 7:
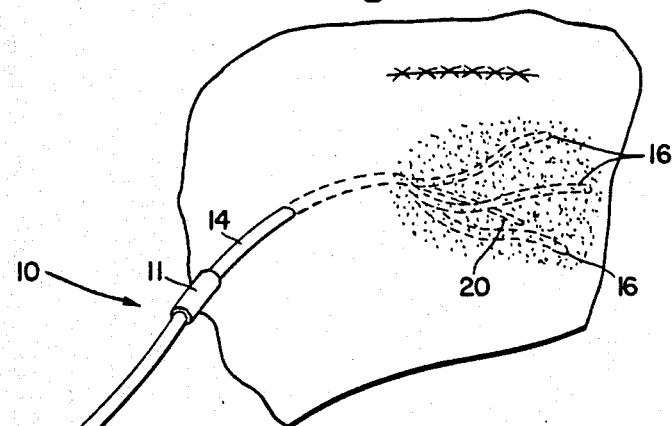
FIG. 7 is a view of an invention surgical drain device in the first phase of postoperative fluid drainage from a wound cavity.
Figure 8:
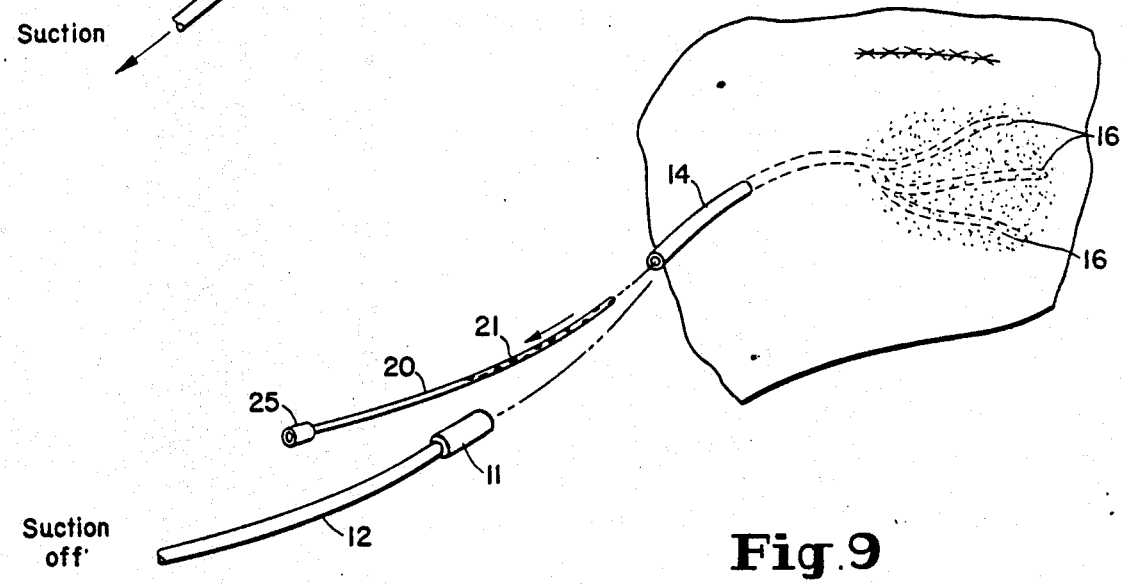
FIG. 8 is a view of the invention surgical drain device of FIG. 7 as it is being disassembled to remove the inner tubular catheter member.
Figure 9:
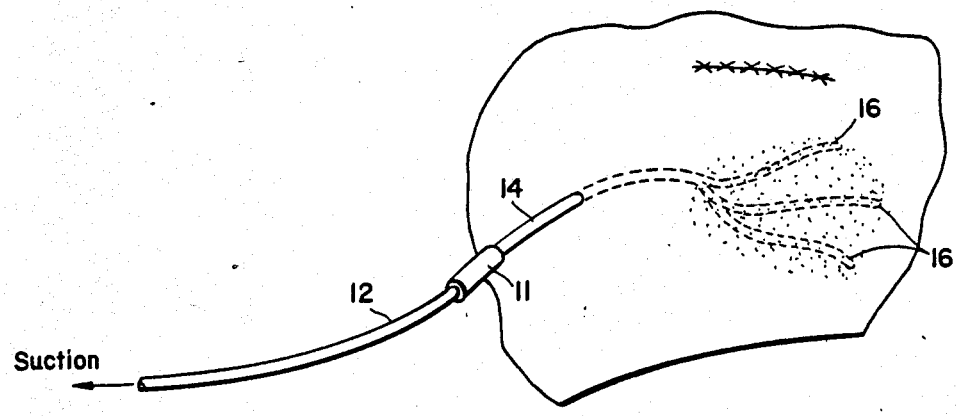
FIG. 9 is a view of the invention surgical drain device of FIG. 7 without the inner tubular catheter member, and with the second stage of postoperative fluid and coagulant solids drainage from the wound cavity by means of the outer tubular member and its radially distributed pliable tail strips, and the attached suction system.

In FIG. 2, outer tubular member 14 has its distal periphery 15 connected with tail strips 16. Inner tubular member 20 is slidably situated within the lumen cross-section of outer tubular member 14. The distal end of inner tubular member 20 has a plurality of drainage ports 21.

In FIG. 3, inner tubular member 20 has a rim-flanged proximal end 25.

In FIG. 5, rim-flanged proximal end 25 of inner tubular member 20 is in abutting contact 26 with proximal end 27 of outer tubular member 14.

After a surgical operation is completed, surgical drain device 10 is manipulated into the patient's wound cavity through the wound or a separate stab wound, and a closed vacuum fluid drainage system is established. The first phase of the wound drainage is conducted during about the first hour of the postoperative period. During the first phase, body fluids are withdrawn from the wound cavity through drainage ports 21 of inner tubular member 20 (i.e., the catheter).

If necessary because of clogging, inner tubular catheter member 20 can be removed for cleaning or for replacement with a second catheter, and the first phase drainage continued.

The second phase of the wound drainage is conducted for a postoperative period of up to about 72 hours, or until fluids cease to flow. Prior to the second phase, inner tubular member 20 is removed, and suction line 12 is attached with sleeve 11 to outer tubular member 14. Postoperative body fluids and coagulated blood and particulate tissue solids are withdrawn along the spaced paths of radially distributed tail strips 16, and through the lumen of outer tubular member 14.

What is claimed is:

1. A polyfunctional surgical drain device for a closed wound drainage system which comprises (1) an outer elongated flexible tubular member; (2) a detachably removable inner elongated flexible tubular member which is in a coextensive and slidable relationship with the outer tubular member, wherein the outer tubular member has one or more thin pliable tail strips extending from the distal end periphery, and the inner tubular member is a catheter with a central lumen and a plurality of perforated drainage ports and with the distal end extending beyond the distal end of the outer tubular member, and the catheter has a rim-flanged proximal end which is in abutting contact with the proximal end periphery of the outer tubular member; and (3) a hollow sleeve member with an end which forms a sealed attachment to the abutting proximal ends of the tubular members, and with an end which is adapted to connect with a suction drainage fluid reservoir.

2. A wound drain device in accordance with claim 1 wherein the outer tubular member has 2-5 thin pliable tail strips extending from the distal end periphery.

3. A wound drain device in accordance with claim 1 wherein the outer tubular member has at least three thin pliable tail strips extending from the distal end periphery.

4. A surgical drain device in accordance with claim 1 wherein the device members are constructed of biocompatible synthetic polymeric material.

5. A polyfunctional surgical wound drainage system which comprises (1) an outer elongated flexible tubular member; (2) a detachably removable inner elongated flexible tubular member which is in a coextensive and slidable relationship with the outer tubular member, wherein the outer tubular member has one or more thin pliable tail strips extending from the distal end periphery, and the inner tubular member is a catheter with a central lumen and a plurality of perforated drainage ports and with the distal end extending beyond the distal end of the outer tubular member, and the catheter has a rim-flanged proximal end which is in abutting contact with the proximal end periphery of the outer tubular member; and (3) a suction drainage fluid reservoir which is attached to the abutting proximal ends of the tubular members with a hollow sleeve means that forms a sealed connection for a vacuum-tight system.

6. A surgical wound drainage system in accordance with claim 5 wherein the outer tubular member has 2-5 thin pliable tail strips extending from the distal end periphery.

7. A surgical wound drainage system in accordance with claim 5 wherein the outer tubular member has at least three thin pliable tail strips extending from the distal end periphery.

8. A surgical wound drainage system in accordance with claim 5 wherein the lumen pathway for the wound drain fluid is smooth walled and ridge-free.

9. A process for multiphasic surgical wound drainage which comprises (1) connecting a suction drainage fluid reservoir to a drain device which is inserted in a surgical wound or body cavity, wherein said drain device comprises an outer elongated flexible tubular member and a detachably removabe inner elongated flexible tubular member which is in a coextensive and slidable relationship with the outer tubular member, wherein the outer tubular member has one or more thin pliable tail strips extending from the distal end periphery and radially distributed within the wound cavity zone, and the inner tubular member is a catheter with a central lumen and a plurality of perforated drainage ports and with the distal end extending beyond the distal end of the outer tubular member, and the catheter has a rim-flanged proximal end which is in abutting contact with the proximal end periphery of the outer tubular member; (2) applying suction to the drain device to withdraw postoperative body fluids from the wound cavity through the catheter member; (3) disconnecting the suction drainage fluid reservoir from the drain device, and detaching and removing the catheter out of the central lumen of the outer tubular member; and (4) connecting the suction drainage fluid reservoir to the proximal end of outer tubular member of the drain device which remains inserted in the wound cavity, and applying suction to the said tubular member of the drain device to withdraw postoperative body fluids and coagulated blood and particulate tissue solids along the spaced paths of the tail strips and through the lumen of said tubular member.

10. A process in accordance with claim 9 wherein the outer tubular member of the drain device has 2-5 thin pliable tail strips extending from the distal end periphery.

11. A process in accordance with claim 9 wherein the outer tubular member of the drain device has at least three thin pliable strips extending from the distal end periphery.

12. A process in accordance with claim 9 wherein the step (2) suction withdrawal of body fluids is conducted during about the first hour of the postoperative period.

13. A process in accordance with claim 9 wherein the first catheter is removed and replaced with a second catheter and the suction withdrawal of body fluids is continued.

14. A process in accordance with claim 9 wherein the step (4) suction withdrawal of postoperative body fluids and coagulated solids is conducted for a period of up to about 72 hours, or until there is cessation of fluid flow.

* * * * *